United States Patent [19]

Bronstein et al.

[11] Patent Number: 4,931,223

[45] Date of Patent: Jun. 5, 1990

[54] METHODS OF USING CHEMILUMINESCENT 1,2-DIOXETANES

[75] Inventors: Irena Y. Bronstein, Newton; John C. Voyta, North Reading, both of Mass.

[73] Assignee: Tropix, Inc., Bedford, Mass.

[21] Appl. No.: 213,344

[22] Filed: Jun. 30, 1988

Related U.S. Application Data

[63] Continuation-in-part of Ser. No. 889,823, Jul. 24, 1986, and a continuation-in-part of Ser. No. 140,035, Dec. 31, 1987, and a continuation-in-part of Ser. No. 140,197, Dec. 31, 1987, abandoned.

[51] Int. Cl.$^5$ .................. C07D 305/04; C07D 407/04
[52] U.S. Cl. ........................................ 252/700; 435/4; 435/5; 435/7; 436/537
[58] Field of Search ............... 252/700; 435/4, 5, 7; 436/537; 549/23, 332, 401, 404; 546/18; 560/117, 138; 568/326

[56] References Cited

U.S. PATENT DOCUMENTS 3,720,622  3/1973  Bollyky ............................. 252/700
4,663,278  5/1987  DiNello ............................. 435/7

OTHER PUBLICATIONS

Zaklika, "Mechanisms . . .", Photochem. Photobiol. 30, 35 (1979).
Zaklika, "Mechanisms . . .", J. Amer. Chem. Soc. 100, 4916 (1978).
Schaap, "Chemiluminescence . . .", J. Amer. Chem. Soc., 104, 3504 (1982).
Schaap, "Substituted Effects . . .", Tetrahedron Lett. 2943 (1982).
Adam et al., "Thermal Stability . . .", Chem. Ber., 116, 839 (1983).

*Primary Examiner*—Mary C. Lee
*Assistant Examiner*—Catherine Scalzo
*Attorney, Agent, or Firm*—Lyon & Lyon

[57] ABSTRACT

Processes are disclosed in which light of different wavelengths is simultaneously released from two or more enzymatically decomposable chemiluminescent 1,2-dioxetane compounds, said compounds being configured, by means of the inclusion of a different light emitting fluorophore in each of them, to each emit light of said different wavelengths, by decomposing each of said compounds by means of a different enzyme. Such processes can be used in multi-channel assays—immunoassays, chemical assays and nucleic acid probe assays—to detect the presence or determine the concentration of chemical or biological substances, and in multi-channel chemical/physical probe procedures for studying the microstructures of macromolecules.

19 Claims, No Drawings

METHODS OF USING CHEMILUMINESCENT 1,2-DIOXETANES

This application is a continuation-in-part of copending Bronstein U.S. patent application Ser. No. 889,823, "Method of Detecting a Substance Using Enzymatically-Induced Decomposition of Dioxetanes", filed July 24, 1986; Bronstein et al U.S. patent application Ser. No. 140,035, "Dioxetanes for Use in Assays", filed Dec. 31, 1987 and Edwards U.S. patent application Ser. No. 140,197, "Synthesis of 1,2-Dioxetanes and Intermediates Therefor", filed Dec. 31, 1987, now abandoned.

FIELD OF THE INVENTION

This invention relates to improved methods of using chemiluminescent compounds, and especially enzymatically cleavable chemiluminescent 1,2-dioxetane compounds. More particularly, this invention relates to the generation and detection of electromagnetic energy released by the decomposition of enzymatically cleavable and chemically cleavable chemiluminescent 1,2-dioxetane compounds used to determine the presence, concentration or structure of substances in a sample, especially an aqueous sample, particularly when such chemiluminescent compounds are used to detect the presence or determine the concentration of chemical or biological substances by art-recognized immunoassay techniques, chemical assays or nucleic acid probe assays, or when they a: used as direct chemical/physical probes for studying the molecular structures or microstructures of various macromolecules: synthetic polymers, proteins, nucleic acids and the like.

BACKGROUND OF THE INVENTION

The decomposition of chemiluminescent chemical compounds to release electromagnetic energy, and especially optically detectable energy—usually luminescence in the form of visible light—is well known and understood. The incorporation of such light emitting reactants in art-recognized immunoassays, chemical assays, nucleic acid probe assays and chemical/physical probe techniques as the means by which the analyte, a substance whose presence, amount or structure is being determined, is actually identified or quantified has assumed increasing importance in recent years, particularly with the advent of enzymatically-cleavable 1,2-dioxetanes; see, for example, the abovementioned copending Bronstein, Bronstein et al and Edwards applications.

SUMMARY OF THE INVENTION

The present invention is based upon the discovery that by using two or more enzymatically cleavable (decomposable) chemiluminescent 1,2-dioxetane compounds, such as those disclosed in the abovementioned copending Bronstein, Bronstein et al and Edwards applications, such compounds being configured, by means of the inclusion of a different light-emitting fluorophore moiety in each molecule, to emit light of a different wavelength from the other(s) upon decomposition [e.g., one such compound can contain a fluorophoric coumarin (benzopyranyl) residue unsubstituted except for a labile ring substituent such as a phosphate ester or acetate ester group, e.g., dispiro(adamantane-2)-3'-(1',2'-dioxetane)-4',2''-(7phosphoryloxy-3''-chromene) sodium salt; see the abovementioned copending Bronstein et al application, the other(s) a labile ring substituent-containing fluorophoric trifluoromethyl-or benzothiazolylbenzopyranyl residue], and each such compound being structured so as to be cleavable by a different enzymatic cleaving means [e.g., one such compound can contain, as mentioned above, a phosphate ester group cleavable by a phosphatase or an acetate ester group cleavable by a carboxylesterase, the other(s) can contain an $\alpha$-D- or $\beta$-D-glucoside group cleavable by a glucose oxidase or a $\beta$-D-galactoside group cleavable by a $\beta$-galactosidase], light of different wavelengths can be induced simultaneously or sequentially by the decomposition of these differently configured and differently decomposable chemiluminescent compounds. Hence, multi-channel assays can be designed in which different enzymes attached to or associated with two or more different analytes will, by cleaving different enzyme cleavable dioxetane substituents, induce the emission of light of a different wavelength for each analyte being assayed.

Further, the emission of light of different wavelengths by a multiplicity of decomposable chemiluminescent compounds, e.g., in multi-channel assays, can also be accomplished by using one or more enzymatically cleavable chemiluminescent 1,2-dioxetane compounds and one or more chemically or electrochemically cleavable chemiluminescent compounds, such as the chemically cleavable analogs of the enzymatically cleavable 1,2-dioxetanes disclosed in the abovementioned Bronstein, Bronstein et al and Edwards applications which for example contain, instead of an enzyme cleavable group, a chemically cleavable group such as a hydroxyl group, an alkanoyl or aroyl ester group such as an acetoxy group, or an alkyl or aryl silyloxy group such as a t-butyldimethylsilyloxy or t-butyldiphenylsilyloxy group, together with one or more enzymes and one or more chemical cleaving means, each attached to a different substance, e.g., an analyte, to once again induce the emission of light of a different wavelength from each such decomposable chemiluminescent compound, e.g., for each analyte being assayed in a multichannel assay.

It is, therefore, an object of this invention to provide improved methods of using chemiluminescent 1,2-dioxetane compounds, and especially enzymatically cleavable chemiluminescent 1,2-dioxetane compounds.

A further object of this invention is to provide improved methods of inducing the simultaneous generation of light of different wavelengths by decomposing differently configured and differently decomposable chemiluminescent compounds, including chemiluminescent 1,2-dioxetane compounds and, in particular, enzymatically cleavable chemiluminescent 1,2-dioxetane compounds.

A still further object of this invention is to provide multi-channel assays carried out in the presence of at least two differently configured and differently decomposable chemiluminescent compounds, including chemiluminescent 1,2-dioxetane compounds and, in particular, enzymatically cleavable chemiluminescent 1,2-dioxetane compounds, as substrates, each of which compounds emits light of a different wavelength from the other(s) and each of which has a labile substituent cleavable by a different means from the other(s), to detect the presence or determine the concentration, by art-recognized immunoassay, chemical assay and nucleic acid probe assay techniques, of chemical or biological substances, and to elucidate the molecular structures or microstructures of various macromolecules:

synthetic polymers, proteins, nucleic acids and the like, by art-recognized direct chemical/physical probe techniques.

These and other objects, as well as the nature, scope and utilization of this invention, will become readily apparent to those skilled in the art from the following description and the appended claims.

DETAILED DESCRIPTION OF THE INVENTION

The enzymatically cleavable chemiluminescent 1,2-dioxetane compounds disclosed and claimed in the abovementioned Bronstein, Bronstein et al and Edwards applications can be represented by the general formula:

In this formula the symbol $R_1$ represents hydrogen, or a bond when $R_2$ represents a substituent bound to the dioxetane ring through a spiro linkage, or an organic substituent that does not interfere with the production of light and that satisfies the valence of the dioxetane ring carbon atom to which it is attached to result in a tetravalent dioxetane ring carbon atom, such as an alkyl, aryl, aralkyl, alkaryl, heteroalkyl, heteroaryl, cycloalkyl or cycloheteroalkyl group, e.g., a straight or branched chain alkyl group having from 1 to 7 carbon atoms, inclusive; a straight or branched chain hydroxyalkyl group having from 1 to 7 carbon atoms, inclusive, or an —OR group in which R is a $C_1$-$C_{20}$ unbranched or branched, unsubstituted or substituted, saturated or unsaturated alkyl, cycloalkyl, cycloalkenyl, aryl, aralkyl or aralkenyl group, any of which may additionally be fused to $R_2$ such that the emitting fragment contains a lactone ring, a fused ring cycloalkyl, cycloalkenyl, aryl, aralkyl or aralkenyl group, or an N, O or S heteroatom-containing group; or a light-emitting fluorophore-forming fluorescent chromophore group bonded to the dioxetane ring through a single bond or a spiro linkage, i.e., a group capable of absorbing energy to form an excited energy state from which it emits optically detectable energy to return to its original energy state, to which an enzyme-cleavable group is bonded by a bond cleavable by an enzyme to yield an electron-rich moiety bonded to the dioxetane ring, e.g., a bond which, when cleaved, yields an oxygen anion, a sulfur anion or a nitrogen anion, and particularly an amido anion such as a sulfonamido anion. Preferably, $R_1$ is a methoxy group.

The symbol $R_2$ represents hydrogen, or a bond when $R_1$ represents a substituent bound to the dioxetane ring through a spiro linkage, or a light-emitting fluorophore-forming fluorescent chromophore group bonded to the dioxetane ring through a single bond or a spiro linkage, to which an enzyme-cleavable group is bonded by a bond cleavable by an enzyme to yield an electron-rich moiety bonded to the dioxetane ring, e.g., one of the aforementioned bonds which, when cleaved, yields an oxygen, sulfur or nitrogen anion.

The light-emitting fluorophore-forming fluorescent chromophore groups which can be symbolized by $R_1$ or $R_2$ can be the residues of the auxiliary fluorophores listed below, unsubstituted or substituted with one or more non-labile substituents such as a branched or straight chain alkyl group having 1 to 20 carbon atoms, inclusive, e.g., methyl, n-butyl or decyl; a branched or straight chain hetercalkyl group having 1l to 7 carbon atoms, inclusive, e.g., methoxy, hydroxyethyl or hydroxypropyl; an aryl group having 1 or 2 rings, e.g., phenyl; a heteroaryl group having 1 or 2 rings, e.g., pyrrolyl or pyrazolyl; a cycloalkyl group having 3 to 7 carbon atoms, inclusive, in the ring, e.g., cyclohexyl; a heterocycloalkyl group having 3 to 6 carbon atoms, inclusive, in the ring, e.g., dioxane; an aralkyl group having 1 or 2 rings, e.g., benzyl; an alkaryl group having 1 or 2 rings, e.g., tolyl; an electron-withdrawing group, such as a perfluoroalkyl group having between 1 and 7 carbon atoms, inclusive, e.g., trifluoromethyl; a halogen; $CO_2H$, $ZCO_2H$, $SO_3H$, $NO_2$, $ZNO_2$, $C\equiv N$, or $ZC\equiv N$, where Z is a branched or straight chain alkyl group having 1 to 7 carbon atoms, inclusive, e.g., methyl, or an aryl group having 1 or 2 rings, e.g., phenyl; an electron-donating group, e.g., a branched or straight chain $C_1$-$C_7$ alkoxy group, e.g., methoxy or ethoxy: an aralkoxy group having 1 or 2 rings, e.g., phenoxy; a branched or straight chain $C_1$-$C_7$ alkoxy group, e.g., xethoxy or ethoxy; an aralkoxy group having 1 or 2 rings, e.g., phenoxy; a branched or straight chain $C_1$-$C_7$ hydroxyalkyl group, e.g., hydroxymethyl or hydroxyethyl; a hydroxyaryl group having 1 or 2 rings, e.g., hydroxyphenyl; a branched or straight chain $C_1$-$C_7$ alkyl ester group, e.g., acetate; an aryl ester group having 1 or 2 rings, e.g., benzoate; or a heteroaryl group having 1 or 2 rings, e.g., benzoxazole, benzthiazole, benzimidazole or benztriazole.

The symbols $R_1$ and $R_2$, taken together, can be a fused fluorescent chromophore group bonded to the dioxetane ring through a spiro linkage, e.g., one having the general formula:

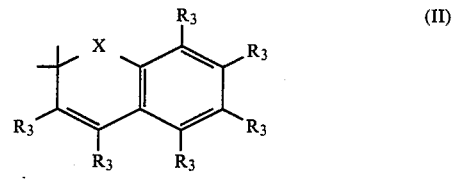

In this formula X is

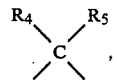

—O—, —S— or —$NR_6$ where each of $R_4$, $R_5$ and $R_6$, independently, is hydrogen, a branched or straight chain alkyl group having 1 to 20 carbon atoms, inclusive, e.g., methyl, n-butyl or decyl, a branched or straight chain heteroalkyl group having 1 to 7 carbon atoms, inclusive, e.g., methoxy, hydroxyethyl or hydroxypropyl; an aryl group having 1 or 2 rings, e.g., phenyl; a heteroaryl group having 1 or 2 rings, e.g., pyrrolyl or pyrazolyl; a cycloalkyl group having 3 to 7 carbon atoms, inclusive, in the ring, e.g., cyclohexyl; a heterocycloalkyl group having 3 to 6 carbon atoms, inclusive, in the ring, e.g., dioxane; an aralkyl group having 1 or 2 rings, e.g., benzyl; an alkaryl group having 1 or 2 rings, e.g., tolyl; or an enzyme-cleavable group as defined above; and each $R_6$, independently, can be hydrogen; an electron-withdrawing group, such as a perfluoroalkyl group having between 1 and 7 carbon atoms, inclusive, e.g., trifluoromethyl; a halogen; $CO_2H$, $ZCO_2H$, $SO_3H$, $NO_2$, $ZNO_2$, $C\equiv N$, or $ZC\equiv N$, where Z is a branched or straight chain alkyl group having 1 to 7 carbon atoms, inclusive, e.g., methyl, or an aryl group having 1 or 2 rings, e.g., phenyl; an electron-donating group, e.g., a branched or straight chain $C_1$-$C_7$ alkoxy group, e.g., methoxy or ethoxy; an aralkoxy group having 1 or 2 rings, e.g., phenoxy; a branched or straight chain $C_1$-$C_7$ hydroxyalkyl group, e.g., hydroxymethyl or hydroxyethyl; a hydroxyaryl group having 1 or 2 rings, e.g., hydroxyphenyl; a branched or straight chain $C_1$-$C_7$ alkyl ester group, e.g., acetate; or an aryl ester group having 1 or 2 rings, e.g., benzoate; a heteroaryl group having 1 or 2 rings, e.g., benzoxazole, benzthiazole, benzimidazole or benztriazole; or hydrogen or an enzyme-cleavable or chemically cleavable group Z as defined herein, with at least one of $R_3$ being an enzyme-cleavable group if no other substituent on the dioxetane ring is a fluorophore group having an enzyme-cleavable substituent. Furthermore, all of the $R_3$ groups together can form a ring which can be substituted or unsubstituted.

The symbol T represents a stablizing group that prevents the dioxetane compound from decomposing before the bond in the labile ring substituent, e.g., the enzyme-cleavable bond in an enzyme-cleavable group, on the light-emitting fluorophore-forming fluorescent chromophore group is intentionally cleaved, such as an unsubstituted or substituted cycloalkyl, aryl, including fused aryl, or heteroaryl group, e.g., an unsubstituted cycloalkyl group having from 6 to 12 ring carbon atoms, inclusive; a substituted cycloalkyl group having from 6 to 12 ring carbon atoms, inclusive, and having one or more substituents which can be an alkyl group having from 1 to 7 carbon atoms, inclusive, or a heteroatom group which can be an alkoxy group having from 1 to 12 carbon atoms, inclusive, such as methoxy or ethoxy, a substituted or unsubstituted aryloxy group, such as phenoxy or carboxyphenoxy, or an alkoxyalkyloxy group, such as methoxyethoxy or polyethyleneoxy, or a cycloalkylidene group bonded to the dioxetane ring through a spiro linkage and having from 6 to 12 carbon atoms, inclusive, or a fused polycycloalkylidene group bonded to the dioxetane ring through a spiro linkage and having two or more fused rings, each having from 5 to 12 carbon atoms, inclusive, e.g., an adamant-2-ylidene group.

One or more of the substituents $R_1$, $R_2$ and T can also include a substituent which enhances the water solubility of the 1,2-dioxetane, such as a carboxylic acid, e.g., acetic acid; sulfonic acid, e.g., methanesulfonic acid or ethanesulfonic acid; or quaternary amino salt group, e.g., ammonium bromide, and at least one of $R_1$ and $R_2$, and preferably $R_2$, is one of the above-described light-emitting fluorophore-forming chromophore group containing an enzyme-cleavable group, and preferably an enzyme-cleavable phosphate ester group.

Included among the labile ring substituents which can be positioned on a fluorophore group to make up the fluorophore moieties of this invention are substituents which, as indicated above, are cleaved to yield an anion, e.g., an oxygen anion, a sulfur anion, or a nitrogen anion such as a sulfonamido anion. Such substituents can be chemically cleavable: a hydroxyl group, an alkanoyl or aroyl ester group, or an alkyl or aryl silyloxy group, for example, but preferably are enzymatically cleavable. Enzymatically cleavable substituents include phosphate ester groups represented by the general formula:

wherein M+ represents a cation such as alkali metal, e.g., sodium or potassium; ammonium, or a $C_1$-$C_7$ alkyl, aralkyl or aromatic quaternary ammonium cation, $N(R_7)_4+$ in which each $R_7$ can be alkyl, e.g., methyl or ethyl, aralkyl, e.g., benzyl, or form part of a heterocyclic ring system, e.g., pyridinium. The disodium salt is particularly preferred. Such quaternary ammonium cations can also be connected through one of their quaternizing groups to a polymeric backbone, viz.

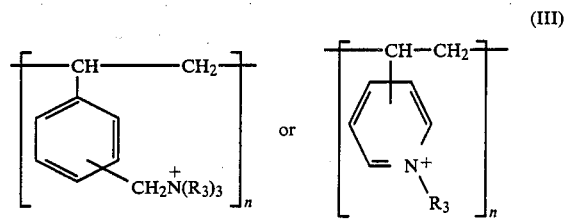

where n is greater than 1, or can be part of a polyquaternary ammonium salt.

Enzymatically cleavable substituents also include enzyme-cleavable alkanoyloxy groups, e.g., an acetate ester group, or an enzyme-cleavable oxacarboxylate group, 1-phospho-2,3diacylglyceride group, 1-thio-D-glucoside group, adenosine triphosphate analog group, adenosine diphosphate analog group, adenosine monophosphate analog group, adenosine analog group, α-D-galactoside group, β-D-galactoside group, α-D-glucoside group, β-D-glucoside group, α-D-mannoside group, β-d-mannoside group, β-D-fructofuranoside group, β-D-glucosiduronate group, p-toluenesulfonyl-L-arginine ester group or p-toluenesulfonyl-L-arginine amide group.

The improved methods of using chemiluminescent 1,2-dioxetanes of this invention are particularly useful when the dioxetanes are employed as the means of identifying or quantifying several analytes using otherwise art-recognized immunoassays, such as those hitherto employed to detect an enzyme or a member of a specific binding pair, e.g., an antigen-antibody pair or a nucleic acid paired with a probe capable of binding to all or a portion of the nucleic acid. Such assays include immunoassays used to detect a hormone such as β-chorionic gonadotropin (β-HCG), thyroid stimulating hormone (TSH), follicle stimulating hormone (FSH), luteinizing hormone (HLH) or the like, cell surface receptor assays, and nucleic acid probe assays used to detect viruses, e.g., HIV or HTLV III, herpes simplex virus (HSV), human papiloma virus (HPV), and cytomegalovirus (CMV), or bacteria, e.g., *E. Coli.*, and histocompatibility assays; for typical assay protocols see working examples I and II, infra, as well as the abovementioned copending Bronstein and Bronstein et al applications. The improved methods of this invention can also be used in assays for chemical analytes, such as, potassium or sodium ions, or in assays for substances such as inter alia. cholesterol and glucose in which the analytes are caused to decompose, for example using an enzyme such as cholesterol oxidase or glucose oxidase, to form a substance, e.g., hydrogen peroxide, capable in combination with another reagent of causing the chemiluminescent compound to decompose.

As noted above, by using two or more chemiluminescent 1,2-dioxetanes that each emit light of a different wavelength from the others, or by using one or more of these different colored light-emitting chemiluminescent 1,2-dioxetanes with one or more other chemiluminescent compounds which emit light of yet other wavelengths, each of such compounds being structured so as to be decomposable by a different means, this invention enables multichannel assays be designed in which different cleaving means, and especially two or more different enzymes, attached to or associated with two or more different analytes will, by cleaving different cleavable dioxetane substituents, induce the emission of light of a different wavelength for each analyte being assayed.

3-(2'-Spiroadamantane)-4-(7''-acetoxy)benzo-2H-pyran-2'-yl-1,2-dioxetane [dispiro(adamantane-2)-3'-(1', 2'-dioxetane)-4', 2''-(7''-acetoxy-3''-chromene)],

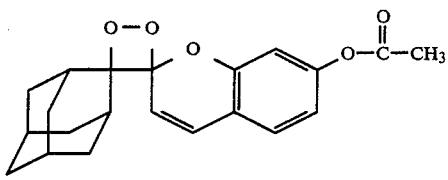

for example, when cleaved with a carboxylesterase, will emit light of 450 nm. (blue), 3-(2'-spiroadamantane)-4-(7''-phosphoryloxy-4'''-trifluoromethyl)benzo-2H-pyran-2'-yl-1,2-dioxetane,

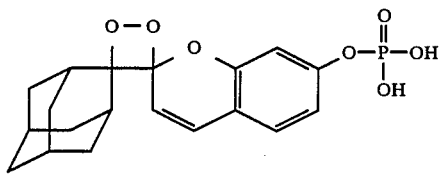

when cleaved with an alkaline phosphatase, will emit light of 480 nm. (cyan, i.e., blue green), and 3-(2'-spiroadamantane)-4-(3'' -benzothiazol 2-yl-7''-β-galactosyloxy)benzo-2H-pyran-2'-yl-1,2-dioxetane,

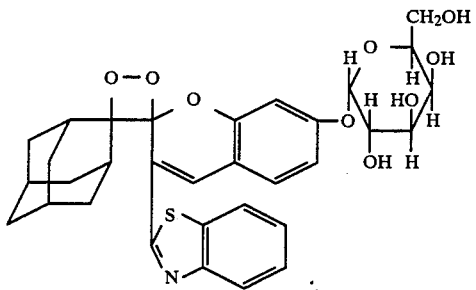

when cleaved with β-galactosidase, will emit light of 515 nm. (green). A simultaneous assay for HLH, FSH and β-HCG, or any two of them, can hence be designed using these three chemiluminescent substances, or any two of them, to produce light emissions of a different color for each of the analytes.

Such an assay can, for example, be a simultaneous sandwich two antibody capture enzyme immunoassay in which a serum or urine sample containing a mixture of analytes: HLH, FSH and β-HCG, for example, or any two of them, is added to a coated matrix containing capture antibodies specific for HLH, FSH and β-HCG and incubated. Next, enzyme labeled antibodies: anti HLH labeled with β-galactosidase, anti FSH labeled with alkaline phosphatase and anti β-HCG labeled with acetylesterase, are added, followed by, e.g., a mixture of the aforementioned three chemiluminescent 1,2-dioxetane substrates: the acetoxybenzopyranyl dioxetane cleavable with acetylesterase, the phosphoryloxybenzopyranyl dioxetane cleavable with alkaline phosphatase and the β-galactosyloxybenzopyranyl dioxetane cleavable with β-galactosidase. The resulting light emissions can be detected either with three different monochromators or on black and white photographic film with three different color filters, with the intensity of the light emissions being a function of the various analyte concentrations.

A homogeneous assay using, e.g., these same three chemiluminescent 1,2-dioxetane substrates can be carried out by first adding a mixture of the analytes ($Ag_1$, $Ag_2$, $Ag_3$) to a mixture of specific Anti $Ag_1$, Anti $Ag_2$ and Anti $Ag_3$ antibodies and small quantities of each of the three analytes bound to the three different enzymes: $Ag_1$-β-galactosidase, $Ag_2$-alkaline phosphatase, $Ag_3$-acetylesterase, and incubating.

Since in anti $Ag_1$ $Ag_1$-β-galactosidase, Anti $Ag_2$ $Ag_2$-alkaline phosphatase and Anti $Ag_3$ $Ag_3$-acetylesterase complexes the enzyme will be inactivated and hence unable to induce luminescence, only enzyme labeled antigens that are unbound will cleave the substrates to emit light. The emitted light can be detected in the same manner as in the above-described sandwich assay. Since there is a competition between native antigens and enzyme labeled antigens, the intensity of the light emitted will be a function of unbound labeled antigens, and thus will correspond to the concentrations of the analytes measured.

Light of various colors emitted when using the improved methods of this invention to identify or quantify various analytes can also be used to make a permanent record of such emissions on color photographic emulsions as well as on specially sensitized black and white high speed films. And, these improved methods can be used to achieve a matched response by detectors: charged coupled devices (CCD's) or silicor photodiodes, for example, having maximum sensitivity for a color other than blue, e.g., green or red. Further, by using chemiluminescent 1,2dioxetanes together with a light absorbing/light shifting auxiliary fluorophore/light enhancer substance which absorbs light of one wavelength and in turn emits light of a different wavelength, e.g., a phycobiliprotein (phycobiliproteins are naturally-occurring substances in which a fluorophore is bonded to a protein), such as phycocyanine or phycoallocyanine, that will absorb the green light emitted by one such substance that emits light in this region of the spectrum and reemit this light as red light, matched responses by color photographic emulsions that exhibit a poor response to blue light, a better response to green light but the best response to red light can also be achieved.

Besides the phycobiliproteins, other auxiliary fluorophores extraneous to the light-emitting fluorophores produced by the decomposition of the chemiluminescent 1,2-dioxetane compounds used in the method of this invention that will accept energy, especially light, from these light-emitting fluorophores and in turn emit detectable energy, again preferably light, can be used when practicing this invention. Among such auxiliary fluorophores that can be used, alone or in combination, are the following substances whose residues can be present in known chemiluminescent 1,2-dioxetanes, such as those disclosed in the abovementioned copending Bronstein, Bronstein et al and Edwards applications, as fluorescent chromophore groups:

anthracene and anthracene derivatives, e.g., 9,10-diphenylanthracene, 9-methylanthracene, 9-anthracene carboxaldehyde, anthrylalcohols and 9-phenylanthracene;

rhodamine and rhodamine derivatives, e.g., rhodols, tetramethyl rhodamine, tetraethyl rhodamine, diphenyldimethyl rhodamine, diphenyldiethyl rhodamine and dinaphthyl rhodamine;

fluorescein and fluorescein derivatives, e.g., 5-iodoacetamido fluorescein, 6-iodoacetamido fluorescein and fluorescein-5-maleimide;

coumarin and coumarin derivatives, e.g., 7-dialkylamino-4-methylcoumarin, 4-bromomethyl-7-methoxycoumarin and 4-bromomethyl-7-hydroxy coumarin;

erythrosin and erythrosin derivatives, e.g., hydroxy erythrosins, erythrosin-5-iodoacetamide and erythrosin-5-maleimide;

aciridine and aciridine derivatives, e.g., hydroxy aciridines and 9-methyl aciridine;

pyrene and pyrene derivatives, e.g., N-(1-pyrene) iodoacetamide, hydroxy pyrenes and 1-pyrenemethyl iodoacetate;

stilbene and stilbene derivatives, e.g., 6,6'-dibromostilbene and hydroxy stilbenes;

naphthalene and naphthalene derivatives, e.g., 5-dimethylamino naphthalene-1-sulfonic acid and hydroxy naphthalenes;

nitrobenzoxadiazoles and nitrobenzoxadiazole derivatives, e.g., hydroxy nitrobenzoxadiazoles, 4-chloro-7-nitrobenz-2-oxa-1,3-diazole, 2-(7-nitrobenz-2-oxa-1,3-diazol-4-yl) methylaminoacetaldehyde and 6-(7-nitrobenz-2-oxa-1,3-diazol-4-yl-aminohexanoic acid;

quinoline and quinoline derivatives, e.g., 6-hydroxyquinoline and 6-aminoquinoline;

acridine and acridine derivatives, e.g., N-methylacridine and N-phenylacridine;

acidoacridine and acidoacridine derivatives, e.g., 9-methylacidoacridine and hydroxy-9-methylacidoacridine;

carbazole and carbazole derivatives, e.g., N-methylcarbazole and hydroxy-N-methylcarbazole;

fluorescent cyanines, e.g., DCM (a laser dye), hydroxy cyanines, 1,6-diphenyl-1,3,5-hexatriene, 1-(4-dimethyl aminophenyl)-6-phenylhexatriene and the corresponding 1,3-butadienes;

carbocyanines and carbocyanine derivatives, e.g., phenylcarbocyanine and hydroxy carbocyanines;

pyridinium salts, e.g., 4-(4-dialkyldiaminostyryl)N-methyl pyridinium iodate and hydroxy-substituted pyridinium salts;

oxonols; and resorofins and hydroxy resorofins.

When such auxiliary fluorophores are bonded to a chemiluminescent compound, they are preferably bonded to the portion of the chemiluminescent compound that, upon decomposition, forms a fragment containing the fluorophore portion of the chemiluminescent compound's molecule. In this way energy transfer is enhanced due to the two fluorophores being in close proximity to one another and by beneficial spatial arrangements provided by the rigidity of the microenvironment. Auxiliary fluorophores that are insoluble or partially insoluble in aqueous medium can be solubilized by first grafting them onto solubilizing molecules, e.g., water soluble oligomer or polymer molecules.

And, in all cases, enhancement of the intensity of the light emitted by decomposition of the chemiluminescent 1,2-dioxetane compounds used in the improved methods of this invention carried out in aqueous media can be achieved by the methods disclosed in the aforementioned Voyta et al application.

In order that those skilled in the art can more fully understand this invention, the following examples are set forth. These examples are given solely for purposes of illustration, and should not be considered as expressing limitations unless so set forth in the appended claims. All parts and percentages are by weight, unless otherwise stated.

EXAMPLE I

A dual channel assay for Human Chorionic Gonadotropins ($\beta$-chain), $\beta$-HCG, and Human Luteinizing Hormones, HLH, is carried out as follows:

MATERIALS

A round nylon membrane (approximately 1 inch in diameter) containing two sets of covalently immobilized capture monoclonal antibodies is used, one set for $\beta$-HCG available from Medix Biotech, Anti HCG, Cat. No. H298-01, and the second for HLH also available from Medix Biotech, Anti LH, Cat. No. L461-09. This nylon membrane is stored in a foil pouch until used.

Mouse monoclonal anti $\beta$-HCG available from Medix Biotech, Cat. No. H298-12, is conjugated with alkaline phosphatase using the glutaraldehyde coupling procedure [Voller, A., et. al., *Bull, World Health Org.*, 53, 55 (1976)]and used as a detection antibody for $\beta$-HCG.

Mouse monoclonal anti HLH available from Medix Biotech, Cat. No. L461-03, is conjugated to carboxylesterase also using the glutaraldehyde coupling procedure referenced above, and used as a detection antibody for HLH.

The substrate buffer solution contains 0.05M carbonate, 1 mM $MgCl_2$, 0.1% by weight BSA (pH=0.5) and 3-(2'spiroadamantane)-4-methoxy-4(3'-phosphoryloxy)-phenyl-1,2-dioxetane disodium salt, (50 $\mu$g/ml), and 3-(2'-spiroadamantane)-4-(3"-benzothiazol-2-yl-7"-$\beta$-galactosyloxy)benzo-2H-pyran-2'-yl-1,2-dioxetane, (50 $\mu$g/ml) as the chemiluminescent substrates.

The wash buffer contains 0.05M carbonate, 1 mM $MgCl_2$ and 2% by weight BSA (pH=9.5).

ASSAY PROCEDURE

Five drops of a previously collected urine sample are placed onto the center of the assay membrane and allowed to soak into the membrane. Next, five drops of a solution containing $\beta$-HCG and HLH conjugated detection antibodies at a concentration of 0.01 millimolar are added to the assay membrane. The liquid is allowed to soak in for at least one minute. Six drops of the wash buffer are slowly added and allowed to soak in and drain for 30 to 60 seconds. Then, five drops of the buffer solution containing chemiluminescent substrates are added and allowed to soak in for approximately one minute.

The assay membrane is placed in a camera luminometer device equipped with pre-exposed calibration scales for β-HCG and LH.

The chemiluminescent light emission generated as a function of the enzymes, alkaline phosphatase and carboxyl esterase, is imaged through a mask containing two narrow band pass filters (approximately 1 cm in diameter). Kodak Wratten Gelatin Filter No. 115 is used to image green emission from the benzopyranyl 1,2-dioxetane substrate, and Kodak Wratten Filter No. 47B is used to isolate the blue emission from the phenyl dioxetane.

The relative levels of β-HCG and HLH present in the sample are determined by a comparison of the appropriate imaged spot brightness with relevant calibration scales.

EXAMPLE II

A three-channel analysis for Herpes Simplex Virus, (HSV), Cytomegalovirus, (CMV), and Human Papiloma Virus, (HPV) is carried out as follows:

MATERIALS

"Gene Screen Plus", a positively charged nylon membrane (Dupont NEN Products) is used for hybridization.

The following buffers are used for the assay:

HSV DNA PROBE ASSAY

Materials and Buffers

Membrane: Gene Screen Plus membrane.
Buffers: Denaturation Buffer, 0.5 M NaOH
Neutralization Buffer, 0.4 M $NaH_2PO_4$ (pH=2.0)
Loading Buffer, 1 part Denaturation Buffer 1 part Neutralization Buffer
Membrane Wetting Buffer 0.4 M Tris (pH=7.5)

| Membrane Prehybridization Buffer | |
|---|---|
| Substance | Final Concentration |
| 0.5 ml 100 × Denhardt's solution | 5 × |
| 0.5 ml 10% SDS | 0.5% |
| 2.5 ML 20 × SSPE | 5 × |
| 2.0 mg denatured, sonicated salmon sperm DNA | 200 μg/ml |
| $ddH_2O$ | |
| 10 ml | |

| Membrane Hybridization Buffer | |
|---|---|
| Substance | Final Concentration |
| 0.5 ml 100 × Denhardt's solution | 5 × |
| 0.5 ml 10% SDS | 0.5% |
| 2.5 ml 20 × SSPE | 5 × |
| 2.0 mg salmon sperm DNA | 200 μg/ml |
| 2.0 ml 50% Dextran sulfate | 10% |
| — $ddH_2O$ | |
| 10 ml | |

| Wash Buffer I |
|---|
| 1 × SSPE/0.1% SDS |
| 20 ml 20 × SSPE |
| 4 ml 10% SDS |
| 376 ml $ddH_2O$ |
| 400 ml |

| Wash Buffer II |
|---|
| 0.1 × SSPE/0.1% SDS preheated to wash temperature indicated on Technical Data Sheet. |
| 2 ml 20 × SSPE |
| 4 ml 20% SDS |
| 394 ml $ddH_2O$ |
| 400 ml (heated) |

| Wash Buffer III |
|---|
| 0.1 × SSPE/0.1% SDS |
| 2 ml 20 × SSPE |
| 4 ml 10% SDS |
| 394 ml $ddH_O$ |
| 400 ml |

| Wash Buffer IV |
|---|
| 3 mM Tris-HCl (pH 9.5) |
| 0.6 ml 1 M Trizma Base |
| 199.4 ml $ddH_2O$ |
| 200.0 ml |

| Wash Buffer V |
|---|
| 0.1 M Trizma HCl pH 6.0 |
| 100 × Denhart's solution |

Preparation of 100 X Denhart's solution (for 100 mls)

Polyvinylpyrrolidone (2 g; mol. wt. 40 K; PVP-40) and 2 g ficoll are dissolved at a temperature greater than 65° C. but less than boiling. The solution is cooled to approximately 40° C., 2 g BSA are added and the solution is brought up to the final volume of 100 ml with $ddH_2O$, aliquoted and stored at $-20°$ C. BSA is easily denatured and in combination with PVP and ficoll it will not go into solution at all if it is not cooled down to $-40°$ C. Hence, the solution is not heated over 40° C. when thawing for use.

| Preparation of 20 × SSC solution | |
|---|---|
| 20 × SSC (for 100 ml) | |
| 3.0 M Sodium Chloride | 17.4 g |
| 0.3 M Sodium Citrate | 8.8 g |

The volume is brought to 100 ml and the solution filtered through a 0.45 μm nitrocellulose filter and stored at room temperature.

Preparation of 20 X SSPE solution

20 X SSPE pH 7.4 (for 1 liter)
3.6 M NaCl
200 mM Sodium phosphate 23 g dibasic, 5.92g monobasic
20 mM EDTA 7.44 g These materials are dissolved, adjusted to pH 7.4 with 5N NaOH, brought to a volume of 1 liter and the solution is then filtered through a 0.45 μm nitrocellulose filter.

| 1 × TE | |
|---|---|
| 1 × TE buffer | 10 mM Tris (pH 7.) |
| | 1 mM EDTA |
| | Autoclave |

The substrate buffer solution contains 0.05M carbonate, 1 mM $MgCl_2$, 0.1% by weight BSA (Ph=9.5) and 3-(2'-spiroadamantane)-4-methoxy-4-(3-acetoxy)phenyl-1,2-dioxetane disodium salt (50 mg/ml), 3-(2'-spiroadamantane)-4-(7''-phosphoryloxy-4''-trifluoromethyl)benzo-2H-pyran-2'-yl-1,2-dioxetane, (50 mg/ml) and 3-(2'-spiroadamantane)-4-(3''-benzothiazol-2-yl-7''-

β-galactosyloxy)benzo-2H-pyran-2'-yl-1,2-dioxetane (50 mg/ml) as the chemiluminescent substrates.

ASSAY PROCEDURE

Samples (50 µl) containing DNA are denatured by incubation for 10 minutes at room temperature in 200 µl of Denaturation Buffer. Ice cold Neutralization Buffer (250 µl) is then added, and the samples placed on ice.

Nylon membrane is soaked for 15 minutes in Wetting Buffer and then inserted into a vacuum manifold device producing 2 cm diameter spots. Loading Buffer, (200 µl) is then aspirated through each well. The denatured DNA samples are then added to each well and aspirated through the membrane. The manifold is then disassembled and the DNA fixed to the membrane using a UV Transilluminator for 5 minutes. The membrane is then incubated in Prehybridization Buffer at 70° C. for 1 hour.

Dots of membrane from the region to which the sample DNA is applied are punched out and inserted into tubes for the remaining steps of the assay. The following enzyme labeled probes are used: probe for HSV labeled with alkaline phosphatase; probe for HPV labeled with β-galactosidase; probe for CMV labeled with carboxylesterase.

The enzyme labeled probes (50 n of each probe in 200 µl of Hybridization Buffer per tube) are added to each tube and incubated for 2 hours at 70° C. The Hybridization Buffer is removed and 400 µl of Wash Buffer I added and the tubes agitated for 10 minutes at room temperature. Washing is continued by first washing with 400 µl of Wash Buffer II at 50° C. for 30 minutes; then with 400 µl of Wash Buffer III at room temperature for 10 minutes; and then with 200 µl of Wash Buffer IV at room temperature.

The membrane is subsequently rinsed with Wash Buffer V at pH 6.0 and placed on a piece of transparent Mylar polyester film. Then, 200 µl of the Substrate Buffer is added and allowed to soak in.

The assay membrane is placed in a camera luminometer device equipped with pre-exposed calibration scales for HSV, HPV and CMV.

The chemiluminescent light emission generated as a function of the enzymes—alkaline phosphatase, carboxyl esterase and β-galactosidase —is imaged through a mask containing three narrow bandpass Kodak Wrattan gelatin filters (approximately 1 cm in diameter), which isolate the blue emission from the phenyl phosphate dioxetane, the cyan emission from the phosphoryloxytrifluoromethylbenzopyranyl dioxetane and the green emnission from the galactosyloxybenzopyraryl dioxetane, respectively.

The relative levels of HSV, HPV and CMV present in the sample are determined by a comparison of the appropriate image brightness with the relevant calibration scale.

The above discussion of this invention is directed primarily to preferred embodiments and practices thereof. It will be readily apparent to those skilled in the art that further changes and modifications in the actual implementation of the concepts described herein can easily be made without departing from the spirit and scope of the invention as defined by the following claims.

We claim:

1. A process in which light of different wavelengths is simultaneously released from two or more enzymatically, chemically or electrochemically decomposable chemiluminescent 1,2-dioxetane compounds, at least one of said 1,2-dioxetane compounds being an enzymatically decomposable 1,2-dioxetane compound, said 1,2-dioxetane compounds being configured, by means of the inclusion of a different light emitting fluorophore in each of said 1,2-dioxetane compounds, to each emit upon decomposition light of said different wavelengths, which comprises decomposing each of said 1,2-dioxetane compounds by means of one of two or more different enzyme, chemical or electrochemical decomposing means, each of said decomposing means being specific to one of said 1,2-dioxetane compounds, at least one of said decomposing means being an enzyme decomposing means.

2. The process of claim 1 in which each of said compounds is represented by the general formula:

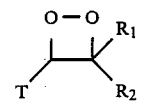

wherein $R_1$ represents hydrogen, or a bond which, together with the indicated bond between $R_2$ and the 4-carbon atom of the dioxetane ring, bonds a substituent represented by $R_2$ to the 4-carbon atom through a spiro linkage, or an organic substituent that does not interfere with the production of light and that satisfies the valence of the dioxetane ring carbon atom to which it is attached, or a light-emitting fluorophore-forming fluorescent chromophore group bonded to the dioxetane ring through a single bond or a spiro linkage, to which an enzymatically, chemically or electrochemically decomposable group is bonded, $R_2$ represents hydrogen, or a bond which, together with the indicated bond between $R_1$ and the 4-carbon atom of the dioxetane ring, bonds a substituent represented by $R_1$ to the 4-carbon atom through a spiro linkage, or a light-emitting fluorophore-forming fluorescent chromophore group bonded to the dioxetane ring through a single bond or a spiro linkage, to which an enzymatically, chemically or electrochemically decomposable group is bonded, at least one of $R_1$ and $R_2$ being such light-emitting fluorophore-forming fluorescent chromophore group, and T represents a stabilizing group that prevents the dioxetane compound from decomposing before the bond in the enzymatically, chemically or electrochemically decomposable group is intentionally cleaved.

3. The process of claim 2 in which the process carried out is a step in an immunoassay.

4. The process of claim 3 in which the immunoassay is for the detection of specific binding pairs comprising an antigen and an antibody.

5. The process of claim 3 in which the labels used in the assay are enzymes.

6. The process of claim 3 in which the labels used in the assay are the chemiluminescent 1,2-dioxetane compounds.

7. The process of claim 3 in which the immunoassay is for the detection of an enzyme.

8. The process of claim 3 in which the immunoassay is for the detection of hormones.

9. The process of claim 2 in which the process carried out is a step in a chemical assay.

10. The process of claim 9 in which the chemical assay is for the detection of chemical substances which, during the assay, are caused to decompose to form substances capable of causing the chemiluminescent 1,2-dioxetane compounds to decompose.

11. The process of claim 10 in which one of the chemical substances is glucose.

12. The process of claim 10 in which one of the chemical substances is cholesterol.

13. The process of claim 2 in which the process carried out is a nucleic acid probe assay.

14. The process of claim 13 in which the nucleic acid probe assay is for the detection of viruses.

15. The process of claim 2 in which the process carried out is a histocompatibility assay.

16. The process of claim 2 in which the process carried out is a technique for studying the microstructure of a macromolecule.

17. The process of claim 2 in which the process carried out is a multi-channel assay carried out in the presence of at least two of the chemiluminescent 1,2-dioxetane compounds as recited in claim 2 as substrates, each of which upon decomposition emits light of a different wavelength from the other(s).

18. The process of claim 17 in which at least one of said chemiluminescent 1,2-dioxetane compounds is chemically decomposable.

19. The process of claim 17 in which at least one of said chemilumenescent 1,2-dioxetane compounds is electrically decomposable.

* * * * *